United States Patent [19]

Rasmussen et al.

[11] Patent Number: 5,324,828
[45] Date of Patent: Jun. 28, 1994

[54] 1-AMINO-1-DEOXYOLIGOSACCHARIDES AND DERIVATIVES THEREOF

[75] Inventors: James R. Rasmussen, Cambridge, Mass.; Jeffrey Davis, Seattle, Wash.

[73] Assignee: Genzyme Corporation, Cambridge, Mass.

[21] Appl. No.: 603,967

[22] Filed: Oct. 26, 1990

Related U.S. Application Data

[63] Continuation of Ser. No. 470,940, Jan. 26, 1990, abandoned, which is a continuation-in-part of Ser. No. 940,574, Dec. 11, 1986, abandoned.

[51] Int. Cl.$^5$ .................. C07H 5/04; C07H 1/00; C12P 19/12; C12Q 1/26
[52] U.S. Cl. ................... 536/18.7; 536/1.1; 536/13.2; 536/28.6; 536/123.1; 536/22.1; 435/101; 435/25; 436/546; 436/545; 530/395
[58] Field of Search ............ 536/18.7, 13.2, 22, 536/18, 27, 1.1; 514/21; 436/545; 252/282; 435/101, 25

[56] References Cited

U.S. PATENT DOCUMENTS

| | | | |
|---|---|---|---|
| 4,065,615 | 12/1977 | Horii et al. | 536/13.2 |
| 4,070,459 | 1/1978 | Huber et al. | 514/21 |
| 4,152,411 | 5/1979 | Schall, Jr. | 436/545 |
| 4,175,123 | 11/1979 | Junge et al. | 536/18 |
| 4,683,298 | 7/1987 | Yalpani | 536/18.7 |
| 4,713,118 | 12/1987 | Barker et al. | 536/1.1 |
| 4,716,222 | 12/1987 | Wallenfels et al. | 536/18.7 |
| 4,719,294 | 1/1988 | Rademacher et al. | 536/18.7 |
| 4,736,022 | 4/1988 | Rademacher et al. | 536/18.7 |
| 4,762,824 | 8/1988 | Kallenius et al. | 536/18.7 |
| 4,948,882 | 8/1990 | Ruth | 536/27 |

OTHER PUBLICATIONS

Risley et al, Jour Biological Chemistry (vol. 260, No. 29) pp. 15488–15494 (1985).
Taga, Eulazio M. et al., Biochemistry 23:815–822 (1984).
Lee, Y. C. et al., The Glycoconjugates, 4:57–83 (1982).
Aplin, John D. et al., CRC Critical Reviews in Biochemistry, pp. 259–306 (1981).
Makino, Mayumi et al., Biochemical and Biophysical Research Communications 24: 961–966 (1966).
Plummer, Thomas et al., The Journal of Biological Chemistry 259:10700–10704 (1984).
Takahashi, Noriko et al., J. Biochem. 84:1467–1473 (1978).
Takasaki, Selichi et al., Methods in Enzymology 83:263–268 (1982).
Tarentino, Anthony L., et al., Biochemistry 24:4665–4671 (1985).
Moczar, E., et al., Carbohydrate Research 50:133–141 (1976).

Primary Examiner—Michael G. Wityshyn
Assistant Examiner—Louise N. Leary
Attorney, Agent, or Firm—William G. Gosz

[57] ABSTRACT

A derivatized 1-amino-1-deoxyoligosaccharide prepared by reacting, at a pH of at least 6.5, a glycopeptide or glycoprotein containing one or more Asn-linked oligosaccharides with a β-aspartylglycosylamine amidohydrolase, and contacting the products with an electrophilic reagent.

3 Claims, 9 Drawing Sheets

R = H, or one or more monosaccharides

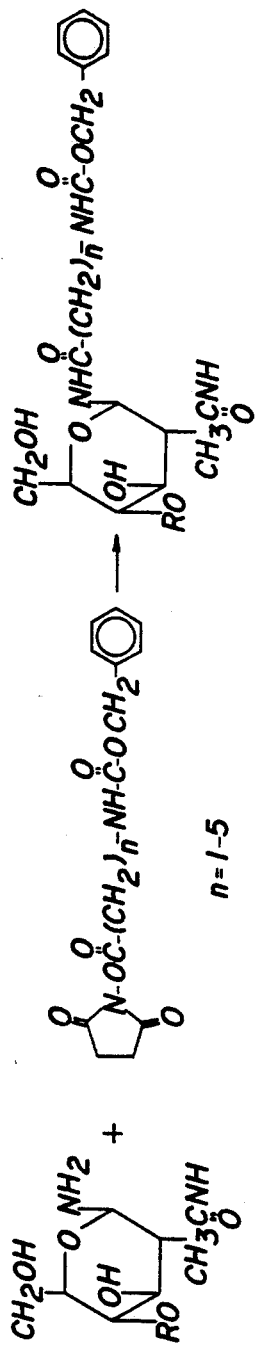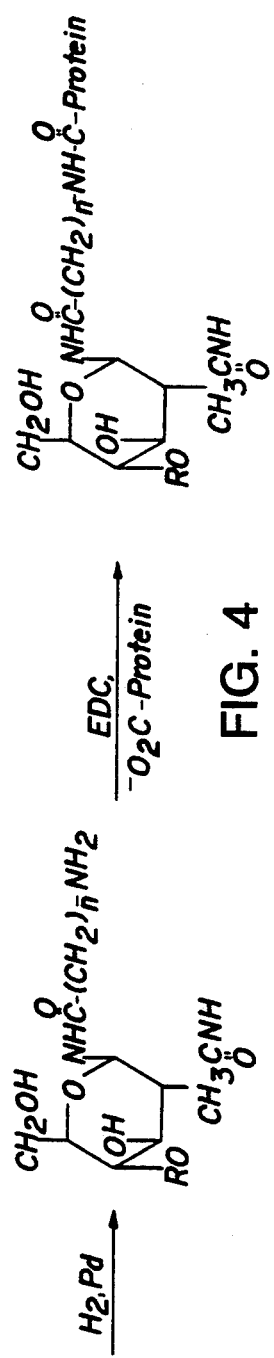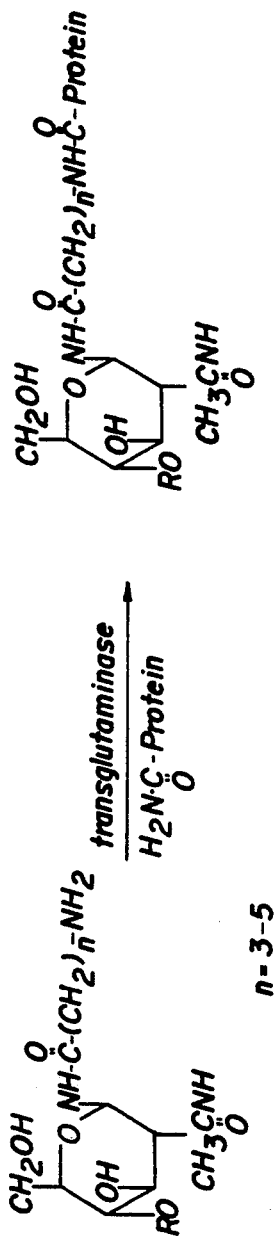
FIG. 4
FIG. 5

5,324,828

1-AMINO-1-DEOXYOLIGOSACCHARIDES AND DERIVATIVES THEREOF

This application is a continuation of U.S. Ser. No. 07/470,940, filed Jan. 26, 1990, now abandoned, which is a continuation-in-part of U.S. Ser. No. 06/940,574, filed Dec. 11, 1986, now abandoned.

BACKGROUND OF THE INVENTION

Certain proteins synthesized by animals, insects, plants and unicellular eukaryotes such as yeast are glycosylated; that is, oligosaccharide chains are covalently attached to the polypeptide backbones. These glycoproteins are primarily localized on the external surface of the plasma membranes of cells and on the lumenal face of intracellular organelles such as lysosomes of the Golgi apparatus. They are also secreted into extracellular fluids.

The carbohydrates moieties of the glycoproteins are believed to be involved in a variety of biological functions, influencing both the biological activity of individual glycoproteins as well as inter- and intracellular recognition events. The carbohydrate units of a particular glycoprotein can modulate the solubility of the protein, protect it from heat denaturation of proteolytic degradation, control its circulatory lifetime, directs its site of uptake in an animal, and influence its antigenicity.

The carbohydrate moieties attached to proteins exposed on the external face of the plasma membrane of cells are believed to be important determinants for biological recognition. They serve as cell surface receptors for certain growth factors, hormones, toxins, viruses, bacteria, and lectins. Cell surface carbohydrates are also involved in the interactions of cells with the extracellular matrix and with other cells.

In view of the known and postulated biological functions of the oligosaccharides of glycoproteins, these carbohydrate units have become the subject of intense interest and experimental investigation. Studies of the carbohydrates include efforts to analyze structure, to determine routes of biosynthesis and catabolism, to examine the specificity of individual enzymes in the metabolic pathways, to modulate the biological activity of glycoproteins by alteration of their carbohydrates, to attach carbohydrates to proteins, and, of course, to determine their biological functions.

Free reducing oligosaccharides obtained from natural sources, and derivatives of the oligosaccharides, have been used extensively for such investigations. For most structural studies, it is desirable to introduce a reporter group such as a radioactive, fluorescent, or UV-active chromophore at the reducing end of the oligosaccharide chain. The most common procedures to accomplish this are reduction with NaB[$^3$H]$_4$ (S. Takasaki and A. Kobata, *Meth. Enzymol*, 50, 50–54 (1978)) or reductive amination with 2-aminopyridine and sodium borohydride. (S. Hase et al., *J. Biochem.* (*Tokyo*), 95, 197–203 (1984)).

The resulting products and similar derivatives are also useful as substrates for studies of the interaction of carbohydrate chains with receptors.

Free reducing oligosaccharides or their derivatives have also been coupled through the reducing sugar to other materials for a variety of purposes. Examples include coupling of the oligosaccharide to a resin for use as an affinity ligand, coupling to a carrier protein in order raise antibodies against carbohydrate, and coupling to a protein to alter the protein's biological activity. Potential improvements in the biological activity of a protein include an increase in solubility, an increase in stability to proteolytic degradation or heat denaturation, a reduction in antigenicity or immunogenicity, an increase or decrease in serum lifetime, or a targeting to a specific cell type in the body such as hepatocytes or macrophages.

Many strategies have been employed for coupling carbohydrates to proteins or other substrates (Y. C. Lee and R. T. Lee, *The Glycoconjugates*, Vol. IV, M. I. Horowitz (Ed.), Academic Press, N.Y., 1982, pp 57–83; J. D. Aplin and J. C. Wriston, Jr. *CRC Crit. Rev.*, 10, 259–306 (1981)). These include, but are not limited to, diazo coupling, thiocarbamylation, amidation, amidination, reductive alkylation, transglutamination and the use of bifunctional reagents such as 2,4,6-trichloro-s-triazine and 2,4-diisocyanotoluene.

The reactions used to prepare the various oligosaccharide derivatives generally result in reduction of the pyranose ring to the open chain (alditol) form or in formation of an O- or S-glycosidic linkage at the reducing end of the oligosaccharide. These derivatization reactions can be difficult to carry out when working with oligosaccharides derived from Asn-linked glycan chains.

The present invention is concerned with enzymatic methods for obtaining 1-amino-1-deoxyoligosaccharides from peptides and proteins containing Asn-linked oligosaccharides and converting them to N-glycoside derivatives that preserve the beta-glycosylamine linkage and the pryanosyl ring of Asn-linked glycoproteins.

SUMMARY OF THE INVENTION

The present invention provides an enzymatic procedure for obtaining 1-amino-1-deoxyoligosaccharides from any glycopeptide or glycoprotein containing Asn-linked oligosaccharides, describes derivatives of the aminodeoxyoligosaccharides that are useful for studies of the structure, biosynthesis, and function of the carbohydrate moieties, and provides procedures for coupling the aminodeoxy sugars to proteins to enhance their biological properties.

BRIEF DESCRIPTION OF THE DRAWINGS

FIG. 4 illustrates the coupling of acyl derivatives of 1-amino-1-deoxyoligosaccharides to the carboxylate groups of a glutamic acid or aspartic acid residue.

FIG. 5 illustrates the coupling of acyl derivatives of 1-amino-1-deoxyoligosaccharides to the amide group of a glutamine residue.

FIG. 7A shows a portion of the $^1$H-NMR spectrum of the TOG prior to hydrolysis by the enzyme. FIG. 7B shows the NAAR signal, after a 1 h incubation of TOG with the enzyme, the reaction was quenched with acetic anhydride. The NMR signal at 5.045 ppm is the anomeric proton for the 1,2-diacetamido intermediate trapped in the beta conformation. The signal partially overlaps the anomeric proton of a mannose residue in the oligosaccharide (5.058 ppm). FIG. 7C shows the HMR signal, after a 4 incubation the quantity of intermediate trapped is much less because of hydrolysis of the aminodeoxyoligosaccharide. The signal at 5.188 ppm is the anomeric proton of the alpha-anomer of the reducing end in the final equilibrated product. FIG. 7D shows the NMR signal for the fully equilibrated carbohydrate moiety from the hydrolysis reaction.

As shown in FIG. 8A, the N-acetyl group at 2,00 ppm is that of the N-acetylglucosamine attached to asparagine. FIG. 8B shows that, upon acetylation a beta-1-acetamido derivative of the 1-amino-N-acetylglucosamine-oligosaccharide intermediate is formed. The NMR signals at 2.002 and 2.000 ppm are those of the 1-acetamido and 2-acetamido groups of the reducing terminal N-acetylglucosamine residue.

DETAILED DESCRIPTION OF THE INVENTION

Preparation of 1-Amino-1-Deoxyoligosaccharides

Procedures exist for the preparation of various glycosylamines by the reaction of ammonia or certain amines with free reducing monosaccharides (for example, H. S. Isbell and H. L. French, *Meth. Carb. Chem.*, Vol. VIII, 255 (1980)). The resulting glycosylamines are stable at alkaline pH, but undergo rapid hydrolysis at pH values between about 4 and 6. In principle it should also be possible to convert free reducing oligosaccharides to glycosylamines by treatment with ammonia.

Figure 1:
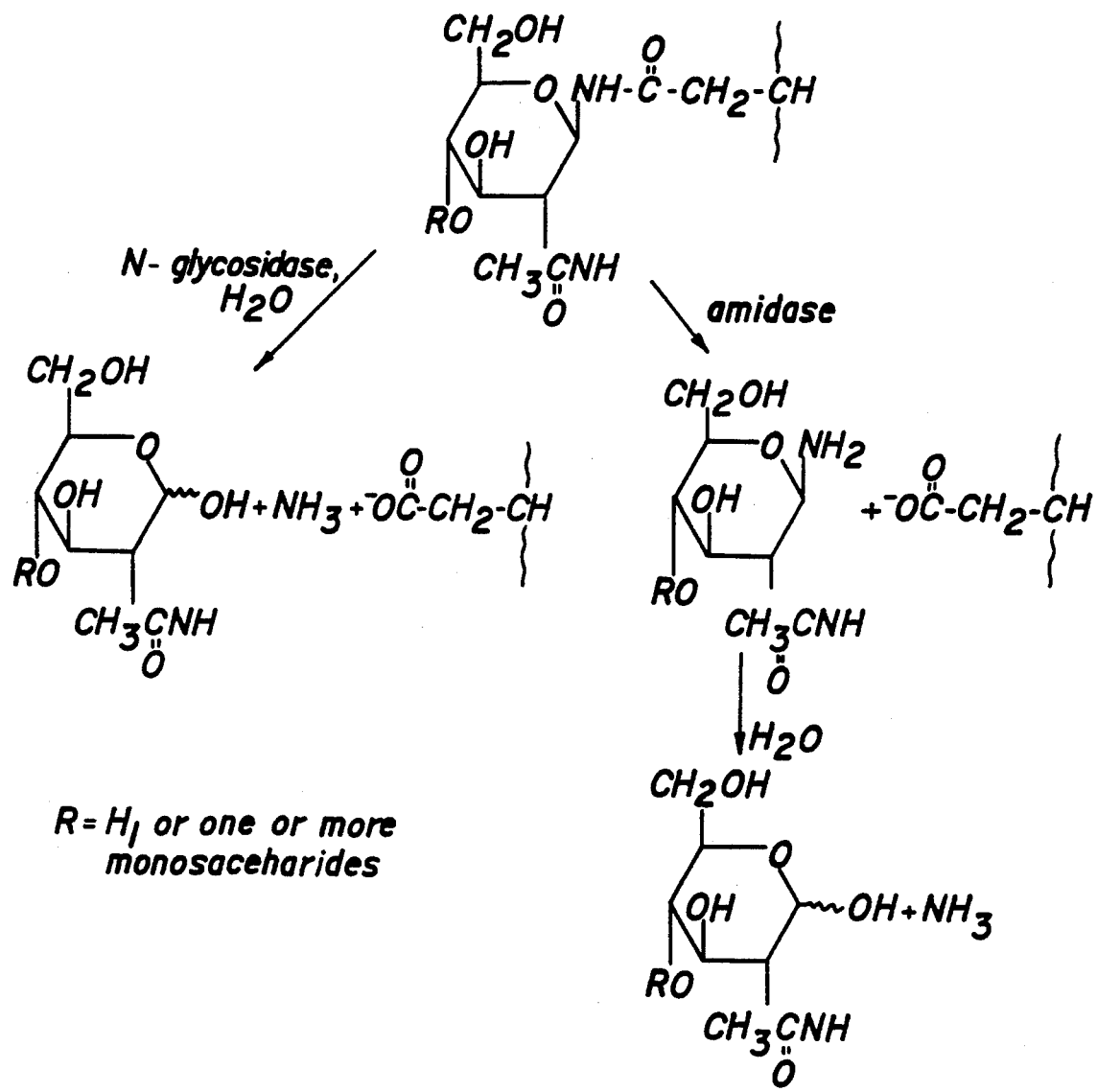
FIG. 1 illustrates the mechanism for hydrolysis of Asn-linked oligosaccharides by amidase and N-glycosidase activities.

The 1-amino-1-deoxyoligosaccharides of the present invention are obtained by treatment of glycopeptides or glycoproteins that contain one or more Asn-linked oligosaccharides with a beta-aspartylglycosylamine amidohydrolase at neutral or alkaline pH. This class of enzyme cleaves the N-acetylglucosaminylaspartate bond to generate an aspartic acid residue and a 1-amino-1-deoxyoligosaccharide. The aminodeoxyoligosaccharide subsequently can undergo a nonenzymatic reaction to release ammonia (FIG. 1). As in the case of the simple glycosylamines, the rate of release of ammonia is pH dependent, being rapid at acidic pH and slow at alkaline pH.

Enzymes with aspartylglycosylamine amidohydrolase activity were first described in the chemical literature in 1965 (E. D. Kavergneva, *Izv. Akad. Nauk S.S.S.R., Ser. Khim.*, 10, 1911 (1965); M. Murakami and E. H. Eylar, *J. Biol. Chem.*, 240, 556 (1965); D. P. J. Tostyon, J. C. Caygill, and F. R. Jeoms, *Biochem. J.*, 97, 43 (1965).) These and similar enzymes from a variety of sources have been shown to be beta-aspartyl N-acetylglucosylamine amidohydrolase (M. Makino et al., *Biochem. Biophys. Res. Comm.*, 24, 961 (1966); A. L. Tarentino and F. Maley, *Arch. Biochem. Biophys.*, 130, 295–302 (1969); J. Conchie and I. Strachan, *Biochem. J.*, 115, 709–715 (1969); J. Conchie et al, *Biochem. J.*, 115, 717–723 (1969)). Their preferred substrate is beta-aspartyl N-acetylglucosamine (Asn-GlcNAc), although certain Asn-oligosaccharides are also hydrolyzed. Substitution of the amino or carboxyl groups of the aspargine gives rise to a substrate that is not hydrolyzed by the enzyme. Thus glycopeptides and glycoproteins are not substrates. The beta-aspartyl N-acetylglucosylamine amidohydrolases are believed to play a role in the catabolic breakdown of Asn-linked oligosaccharides. Deficiency of the human aspartyl N-acetylglucosylamine amidohydrolase, which has been purified to homogeneity from liver (M. M. McGovern et al., *J. Biol. Chem.*, 258, 10743–10747 (1983)), leads to a genetic deficiency disease called aspartylglycosaminuria. Clinical symptoms include mental retardation, facial and skeletal abnormalities, and excretion of high levels of Asn-GlcNAc in the urine.

Aspartyl N-acetylglucosylamine amidohydrolases ache been purified from several sources including pig sera, hen oviduct, rat liver, and human liver. The enzymes generally have a broad pH optimum between 4.0 and 6.0. The reported molecular weight of the proteins varies between 80,000 and 110,000 kD.

Although it was originally believed that the aspartyl N-acetylglucosylamine amidohydrolase cleaved the N-glycosidic bond of the Asn-GlcNAc linkage, it was subsequently proposed that the enzyme is an amidase (FIG. 1). (M. Makino et al., *Biochem. Biophys. Res. Comm.*, 24, 961 (1966)).

The experimental evidence supporting this conclusion is:

1. The observation that at low pH stoichiometric amounts of aspartic acid, ammonia and N-acetylglucosamine are formed, but at alkaline pH, only a small percentage of the expected ammonia is released until the reaction mixture is acidified.
2. The detection of a compound with a chromatographic mobility identical to authentic 1-amino-1-deoxy-N-acetylglucosamine.

Aspartyl N-acetylglucosylamine amidohydrlases that appear to produce an aminodeoxy sugar intermediate include the enzyme from pig sera (M. Makino et al., *Biochem. Biophys. Res. Comm.*, 24, 961 (1966)), hen oviduct (A. L. Tarentino and F. Maley, *Arch. Biochem. Biophys.*, 130, 295–303 (1969), and rat liver (J. Conchie and I. Stracham, *Biochem. J.*, 115, 709–715 (1969)). In addition, it was observed that the enzyme from pig sera hydrolyzed an ovalbumin Asn-oligosaccharide to yield an oligosaccharide had the characteristics of an aminodeoxy derivative.

In 1977, Takahashi (*Biochem. Biophys. Res. Comm.*, 76, 1194–1201 (1977)) described an enzyme isolated from almond emulsin that was capable of cleaving the beta-aspartylglycosylamine linkage present in glycopeptides and certain glycoproteins but not in unsubstituted asparaginyl derivatives. In a subsequent paper, evidence was presented that the hydrolysis of the aspartyl N-acetylglycosylamine linkage preceded the release of ammonia. In that paper the authors concluded that the reaction catalyzed by the almond enzyme was analogous to the two step reaction carried out by the aspartyl N-acetylglucosylamine amidohydrolase and that "although the formation of an intermediate 1-amino-N-acetylglucosamine-oligosaccharide, has not been confirmed, . . . these experimental data support the view that the enzyme is not an N-glycosidase but an amidase." N. Takahashi and H. Nishibe, *J. Biochem.*, 84, 1467–1473 (1978)). This statement notwithstanding, the same enzyme from almond emulsin and a second enzyme from *Flavobacterium meningosepticum* have been termed peptide; N-glycosidases following isolation and characterization (T. H. Plummer, Jr. and A. L. Tarentino, *J. Biol. Chem.*, 256, 10243–10246 (1981); A. L. Tarentino and T. H. Plummer, Jr., *J. Biol. Chem.*, 257, 10776–10780 (1982); Em. M. Tage et al., *Biochemistry*, 23, 815–822 (1984); T. H. Plummer, Jr. et al., *J. Biol. Chem.*, 259, 107000–10704 (1984); A. T. Tarentino et al., *Biochemistry*, 24, 4665–4671 (1985)). The almost enzyme has a broad specificity, being able to hydrolyze the bond between high mannose-, hybrid- and complex-type oligosaccharides and asparaginyl residues in glycopeptides and certain glycoproteins (N. Takahasi and H. Nichibi, *Biochem. Biophys. Acta*, 657, 457–467 (1981); H. Ishihara et al., ibid, 661, 274–279 (1981)). However, the enzyme acts slowly, if at all, on many glycoproteins, preferring glycopeptide substrates (A. L. Tarentino and T. H. Plummer, Jr., *J. Biol. Chem.*, 257, 10776–10780 (1982)).

Although the aspartyl N-acetylglycosylamine amidohydrolase from almond emulsin has nearly the same pH rate profile as the aspartyl N-acetylgucosylamine amidohydrolases described earlier, it differs in several significant ways:

1. Its preferred substrates are glycopeptides;
2. The enzyme is unable to cleave Asn-oligosaccharides;
3. The enzyme has a lower molecular weight (67,000 kD); and
4. Glycopeptides bearing a single monosaccharide (GlcNAc) are not substrates.

An enzyme that appears to be similar to the one from almond emulsin has been detected in jack bean meal (K. Sugujama et al., *Biochem. Biophys. Res. Comm.*, 112 155–160 (1983)).

Finally, an enzyme with "peptide: N-glycosidase" activity has been detected in fermentation broths of *Flavobacterium meningosepticum* (T. H. Plummer, Jr. et al., *J. Biol. Chem.*, 259, 10700–10704 (1984)) and purified to homogeneity (A. L. Tarentino et al., *Biochemistry*, 24, 4665–4671 (1984)).

The flavobacterium enzyme resembles the amidohydrolase from almond emulsin in that it:

1. Prefers glycoproteins and glycopeptides as substrates;
2. Is unable to hydrolyze Asn-oligosaccharides or glycopeptides bearing a single GlcNAc;
3. Has a similar broad specificity toward different oligosaccharides.

However, several significant differences also are apparent. The Flavobacterium enzyme:

1. Is more active in hydrolyzing glycoprotein substrates;
2. Has a much lower molecular weight (35,000 kD); and
3. Has a much higher pH optimum (8.6).

In view of these significant differences, it is possible that the Flavobacterium amidohydrolase has an entirely different mechanism of action. The enzyme does appear to have amidase activity because during cleavage of Asn-oligosaccharides from glycopeptides, the asparagine residue is converted to aspartate (T. H. Plummer, Jr. et al., *J. Biol. Chem.*, 259, 10700–10704 (1984)).We are aware of no studies of the mechanism of the enzyme.

There is a tremendous structural variety in the oligosaccharides linked by asparagine residue to proteins. The present invention can be applied to any that are substrates for an amidohydrolase. It is typical for a glycoprotein to exhibit microheterogeneity with respect to the oligosaccharides present on the molecule. Thus it will usually be necessary to purify either the aminodeoxyoligosaccharide or a derivative if a single homogeneous material is desired. In most cases it will probably prove earlier to purify the derivative. Purification procedures will likely be some form of chromatography such as lectin, gel filtration, ion exchange, silica gel, or reverse phase chromatography.

Examples of relatively homogeneous oligosaccharides that may be obtained directly from glycoproteins without extensive purification include: $H_2N$-GlCNAc-GlcNAc-$Man_9$ from soybeam agglutinin, $H_2N$-GlCNAc-GlcNAc-$Man_{5-8}$ from ribonuclease B, biantennary complex chains from fibrinogen or human transferrin, biantennary complex chains with a proximal fucose residue from bovine IgG, triantennary complex chains from fetuin, and tetraantennary complex chains from $alpha_1$-acid glycoprotein.

The enzymes from almond emulsion and *Flavobacterium meningosepticum* are particularly useful for releasing the aminodeoxyoligosaccharides because they have been purified to homogeneity and are commercially available (Seikagku, Japan; Genzyme Corporation, Boston, Mass.), they have a broad substrate specificity, they can utilize glycopeptides and glycoproteins as substrates, and they are active at neutral and alkaline pH. In the present invention the 1-amino-1-deoxyoligosaccharides produced in the reaction by the amidohydrolases are observed directly for the first time. Furthermore, it is demonstrated that the released amino deoxyoligosaccharides exist largely as the beta-anomer. Finally a 1-amino-1-deoxyoligosaccharide is trapped for the first time as a stable derivative.

Preparation of Derivatives of 1-Amino-1-Deoxyoligosaccharides

It is known that acyl derivatives of glycosylamines can be prepared and that the acylated glycosylamines are generally stable compounds that do not undergo hydrolysis in aqueous solution, (H. S. Isbell and H. L. French, *Meth. Carb. Chem.*, Vol. VIII, 255 (1980)). The Asn-oligosaccharide linkage in glycoproteins is itself an example of a stable acyl derivative of a glycosylamine. To date no aminodeoxyoligosaccharide prepared by enzymatic hydrolysis of a glycopeptide has been converted to an acyl derivative; the starting glycosylamines have previously been prepared through reaction of a free reducing sugar with ammonia.

In the present invention it is demonstrated that it is possible to form acyl derivatives of aminodeoxyoligosaccharides released from glycopeptides and glycoproteins by an amidohydrolase. In general a reactive acyl derivative such as an acid chloride, acid anhydride, or other active acyl compound, a large number of which are well known in the chemical literature, is mixed with the released 1-amino-1-deoxyoligosaccharide at alkaline or neutral pH. To minimize hydrolysis of the glycosylamine, the enzymatic reaction and trapping reaction can be performed in the presence of the hydrolyzed peptide or glycoprotein, but it is preferable to first remove the peptide or polypeptide. This can be accomplished by precipitation of the protein by addition of a solvent such as ethanol, dioxane or tetrahydrofuran. The trapping reaction can be performed in aqueous solution or in mixed solvent such as alcohol/water, tetrahydrofuran/water, dioxane/water, dimethylformamide or dimethyl sulfoxide. A base such as triethylamine, pyridine or sodium bicarbonate may be added to neutralize acid released during the reaction.

In certain instances the trapping reaction can be performed in a manner that produces the desired product directly. In other cases it will be desirable to trap the aminodeoxyoligosaccharide with a bifunctional linker that can itself then be coupled to another material in a subsequent reaction.

Applications of the 1-Amino-1-Deoxyoligosaccharide Derivatives

1. Structural Analysis of Oligosaccharides

Underivatized oligosaccharides are difficult to analyze by conventional means because of the lack of a "reporter" group. Indeed, it is routine procedure to introduce a label such as a fluorescent group or radioactive group to increase sensitivity. Two of the most common labeling procedures involve reductive amination with 2-aminopyridine and sodium borohydride (S. Hase et al., J. Biochem. (Tokyo), 95:197–203 (1984)) and reduction with sodium borotritide (S. Takasaki et al., Meth. Enzymol, 83:263–268 (1982)). Each of these techniques has been employed to analyze oligosaccharides released by aspartaryl N-acetylglycosylamine amidohydrolases, presumably following release of ammonia to generate the free reducing oligosaccharide (I. Ishii et al., *J. Chromat.*, 345, 134–139 (1985)). The labeled oligosaccharides are then analyzed by techniques such as gel filtration chromatography or BioGel P4 columns (K. Yamashita et al., 83, 105–126 (1982)), high pressure liquid chromatography (I. Ishii et al., *J. Chromat.*, 345, 134–139 (1985); J. Baenziger and M. Natowicz, *Anal. Biochem.*, 112, 357–361 (1981); S. J. Mellis and J. Baenziger, *Anal. Biochem.*, 114, 276–280 (1981) and exoglycosidase digestion (K. Yamashita et al., Meth. *Enzymol.*, 83, 105–126 (1982)).

In one embodiment of the present invention, the aminodeoxyoligosaccharides released from glycopeptides or glycoproteins by an amidohydrolase can be trapped directly by a reactive derivative of the reporter group. Examples include, but are not limited to:

1. Formation of dimethylamino-naphthylsulfonamide (Dansyl) derivatives by treatment with dansyl chloride;
2. Formation of fluorescein derivatives by treatment with fluorescein isothiocyanate;
3. Formation of 4-dimethylaminoazobenzene 4-sulfonamide (Dabsyl) derivatives by treatment of an aminodeoxyoligosaccharide with Dabsyl chloride;
4. Formation of N-substituted 1-cyanobenz-[f]isoindole derivatives by treatment with naphthalene 2,3-dicarboxyaldehyde and cyanide;
5. Formation of phenyl isothiocyanate derivatives by treatment with phenyl-isothiocyanate; and
6. Formation of a [$^3$H]- or [$^{14}$C] 1-acetamido-1-deoxyoligosaccharide by treatment of an aminodeoxyoligosaccharide with [$^3$H]- or [$^{14}$C] acetic anhydride.

2. Preparation of Substrates for Glycosyltransferases and Endo- and Exoglycosidases The derivatives of the 1-amino-1-deoxyoligosaccharides described in the previous section also are useful as substrates for glycosyltransferases and exo- and endoglycosidases. Simple mono- and di-saccharides are often used to assay these enzymes (for example, p-nitrophenylglycosides are used to assay exoglycosidases), but the substrate often bind poorly to the enzyme. It would be a significant advantage to perform the assays with oligosaccharides more closely resembling the natural substrates. In addition to accomplishing this objective, the 1-amino-1-deoxyoligosaccharide derivatives of the present invention maintain the beta-glycosylamine linkage and the pyranose form of the N-acetylglucosamine residue previously bonded to the asparagine.

3. Probes for Use in Cell Biology

The various derivatives described above have additional applications in the field of cell biology. These applications include studying the interaction of oligosaccharides with receptors on or isolated from cells, bacteria, or viruses. The derivatives may also be used to localize oligosaccharide binding proteins in tissue slices or whole animals.

4. Formation of Neoglycoproteins

For reasons described earlier, it is of interest to develop methods for attaching oligosaccharides to proteins (thereby forming "neoglycoproteins"). There are several reports on coupling synthetic glycosylamines to a protein by formation of an amide linkage with carboxyl groups of the protein. Wriston (*FEBS Lett.*, 33, 93–95 (1973) treated chymotrypsinogen with 1-ethyl-3-3(3-dimethyl-aminopropyl)carbodiimide (EDC) and synthetic 1-amino-1-deoxyglucose. He reports coupling about three equivalents of aminoglucose to each chymotrypsinogen molecule.

In a series of papers, Moczar and coworkers describe several glycosylamine derivatives of lysozyme prepared by EDC coupling at acidic pH (E. Moczar, *Experientia*, 29, 1576–1577 (1973); E. Moczar and . Leboue, *FEBS Lett.*, 50, 300–302 (1975); E. Moczar and G. Vass, *Carbohydr. Res.*, 50, 133–141 (1976). The glycosylamines that were employed included lactosylamine, glucosylamine, galactosylamine and mannosylamine, each prepared by reaction of the corresponding sugar with ammonia.

The preferred coupling method of the present invention involves trapping the aminodeoxyoligosaccharide with a bifunctional reagent. The derivative is subsequently coupled to the protein. A variety of chemistries, well known in the chemical literature, can be employed to couple the oligosaccharide derivative to the protein. (For example, see Y. C. Lee and T. T. Lee, in *The Glycoconjugates*, Vol. IV; M. I. Horowitz, Ed., Academic Press, 1982, pp 57–83; J. D. Aplin and J. C. Wriston, Jr., *CRC Crit. Rev.*, 10, 259–306 (1981)).

With this method there is a "linker" or "spacer" interposed between the protein and the oligosaccharide. This strategy allows one to employ a wider range of coupling chemistries, minimizes side reactions with the protein, and makes the oligosaccharide more accessible for binding by other molecules.

Figure 2:
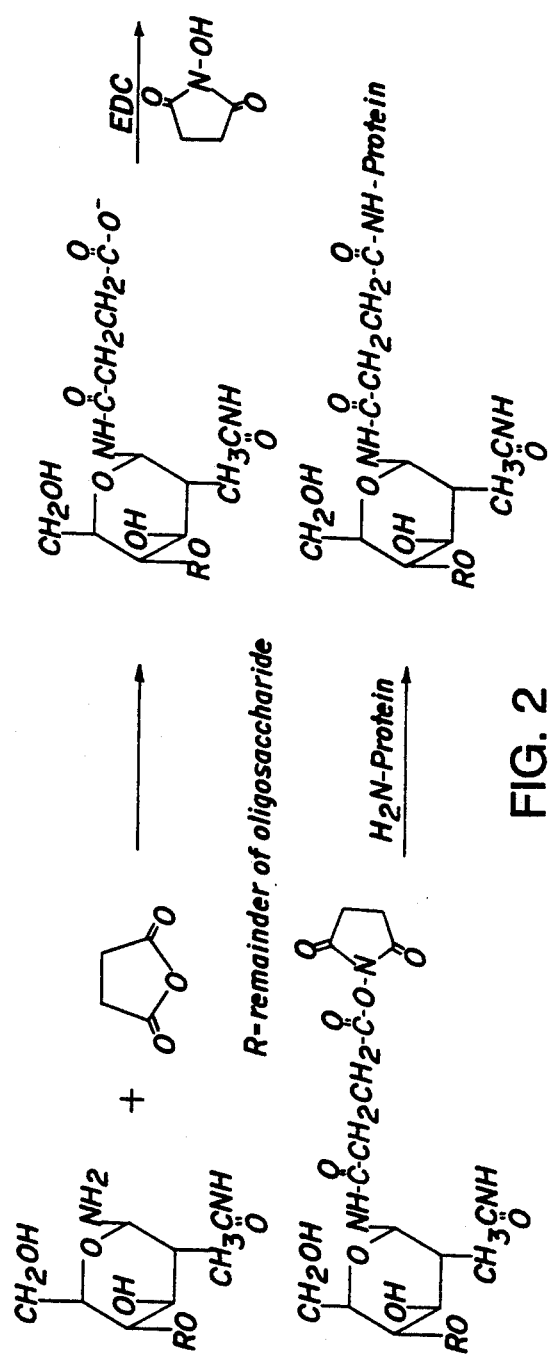
FIG. 2 illustrates the coupling of acyl derivatives of 1-amino-1-deoxyoligosaccharides to the $\epsilon$-amino group of a lysine residue.

Among the amino acids with side chains that it is possible to derivatize are the ε-amino group of lysine, the hydroxyl group of serine, threonine or tyrosine, the thiol group of cysteine, the carboxylate group of aspartic acid or glutamic acid, the imidazole ring of histidine, the aromatic ring of phenylalanine, tryptophan or tyrosine and the amide group of glutamine. The C- and N-terminal groups are also subject to derivatization. Examples of preferred coupling procedures follow below:

a. ε-amino group of lysine and/or the N-terminal amino group of the protein. (FIG. 2).

Figure 3:
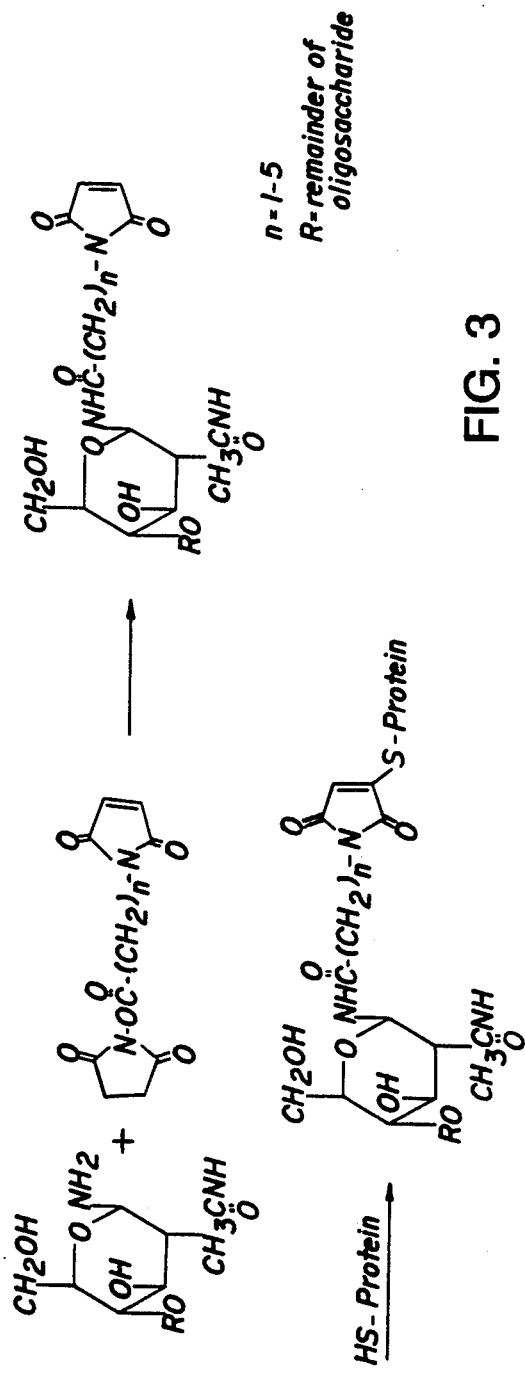
FIG. 3 illustrates the coupling of acyl derivatives of 1-amino-1-deoxyoligosaccharides to the thiol group of a cysteine residue.

The 1-amino-1-deoxyoligosaccharide released by the aminohydrolase is first trapped by treatment with an excess of a cyclic anhydride such as succinic anhydride or glutaric anhydride. The free carboxylic acid group of the linker is then activated by formation of a derivative such as the N-hydroxysuccinimide ester. This activated derivative can then be reacted with the protein of choice.

b. Thiol group of cysteine (FIG. 3).

The 1-amino-1-deoxyoligosaccharide is trapped by treatment with a linker possessing an activated acyl derivative and maleimide moiety. The resulting product can be used to derivatize the protein of choice.

c. Carboxylate groups of aspartic acid, glutamic acid or the C-terminal amino acid (FIG. 4).

The 1-amino-1-deoxyoligosaccharide is trapped by treatment with a linker possessing an activated acyl derivative and a protected amino group. After deprotection, the resulting product can be coupled to the protein with the aid of a coupling reagent such as EDC or carbonyldiimidazole. Although it is also possible to couple the aminodeoxyoligosaccharide directly to the protein as mentioned earlier, the procedure in FIG. 4 has the advantage that one does not have to be concerned with decomposition of the aminodeoxyoligosaccharide to ammonia and the free oligosaccharide at the preferred pH of the reaction with EDC (pH 4 to 6).

d. The amide group of glutamine (FIG. 5).

The

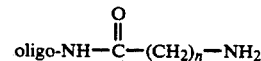

derivative described in FIG. 5 can be substituted for the $NH_2$ group of glutamine through a reaction catalyzed by the enzyme transglutaminase (S. Yan and F. Wold, *Biochemistry*, 23, 3759–3765 (1983)).

One application of the derivatization reaction is to extend the serum lifetime of proteins. For example, it is known that small (30,000 kD) proteins are rapidly cleared from the circulation primarily by the kidney, while larger proteins are removed by other mechanisms. Thus therapeutic proteins such as interleukin-2 have a short serum half-life because of renal clearance. By attaching appropriate oligosaccharides, clearance by the kidney can be prevented. The optimum carbohydrate chains to attach in this case would be complex oligosaccharides, for example, those derived from fibrinogen, transferrin, fetuin or alpha-1-acid glycoprotein. Any of the coupling procedures described earlier could be employed.

A second application of the derivatization reaction is to target proteins to specific cell types. Cells with sugar-specific cell surface receptors can bind proteins in the circulation bearing the complementary carbohydrates and internalize the protein into the cell. There are three well-known sugar binding receptors: the asialoglycoprotein (galactose specific) receptor or hepatocytes, the mannose/N-acetylglucosamine receptor on reticuloendothelial cells, and the fucose receptor on hepatocytes and lymphocytes. (For a review, see E. Neufeld and G. Ashwell, in *The Biochemistry of Glycoproteins and Proteoglycans*, W. Lennarz, Ed., Plenum Press, New York, 1980, 241–266). By coupling appropriate 1-amino-1-deoxyoligosaccharides, a protein can be targeted to each of these cells types. To target a protein to macrophages, the oligosaccharides from a glycoprotein such as soybean agglutinin or ribonuclease B could be employed. To target a protein to cells bearing the asialoglycoprotein receptor, one could employ complex oligosaccharides isolated from fibrinogen, transferrin, fetuin or alpha-1 acid glycoprotein after treatment (neuraminidase or dilute acid) to remove the terminal sialic acid residues.

5. Ligands for resins, beads and surfaces. Using chemistries similar to those described for preparation of neoglycoproteins, it is possible to prepare derivatives of various solid materials such as resins, beads and films. Applications for these derivatized materials include:

a. Use as an affinity resin for purification of receptors, lectins, glycosyl-transferases, and glycosidases.

b. Use in diagnostic kits for detection of oligosaccharides, receptors, lectins, glycosyltransferases, and glycosidases.

Examples 1 and 2 that follow are taken from J. M. Risley and R. L. van Etten, *J. Biol. Chem.*, 260, 15488–15494 (1985).

EXAMPLE 1

Release of 1-Amino-1-Deoxyoligosaccharides from Turkey Ovomucoid Glycopeptide with Aspartyl N-Acetylglycosylamine Amidohydrolase from Almond Emulsin To a solution of 1 mg of turkey ovomucoid glycopeptide (a heterogeneous mixture of three structurally related complex type oligosaccharides purified as described by E. M. Taga et al., *Biochemistry*, 23, 815–822 (1984)) in 50 mM phosphate, $p^2H$ 7.0 buffer in 99.96% $^2H_2O$ equilibrated at the desired temperature was added the almond amidohydrolase enzyme to give a total volume of 0.5 ml. The reaction was followed by $^1H$ NMR. The hydrolysis of 1-amino-1-deoxy-N-acetylglucosamine in 50 mM phosphate, $p^2H$ 7.0, buffer in 99.96% $^2H_2O$ to 2-acetamido-2-deoxy-D-glucose was followed by $^1H$ NMR as a reference compound. The proton peaks of interest were integrated and the pseudo first-order rate constant was calculated from the slope of a plot of the natural logarithm of the peak area as a function of time.

The two-step hydrolysis reaction of turkey ovomucoid glycopeptide (TOG) to intermediate (INT) to the final carbohydrate product (CHO), which is assumed to be irreversible, is described by two independent reactions

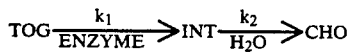

where $k_1$, and $k_2$ are the rate constants for each step. The set of differential equations, which describes the reaction in Equation 1 is $$d[TOG]/dt = -k_1[TOG] \quad (2)$$

$$d[INT]/dt = -k_1[TOG] - k_2[INT]$$

$$d[CHO]/dt = k_2[INT]$$

The differential equations are solved by the variations of parameters method. When the initial concentrations of INT and CHO are zero, the solution reduces to $$[TOG]_1 = [TOG]_0 e^{-k_1 t} \quad (3)$$

$$[INT] = \frac{k_1}{k_2 - k_1}[TOG]_0 (e^{-k_1 t} - e^{-k_2 t})$$

$$[CHO]_1 = [TOG]_0 = \frac{1}{k_2 - k_1}[TOG]_0 (k_1 e^{-k_2 t} - k_2 e^{-k_1 t})$$

where [TOG] is the initial concentration of the enzyme substrate.

Figure 6:
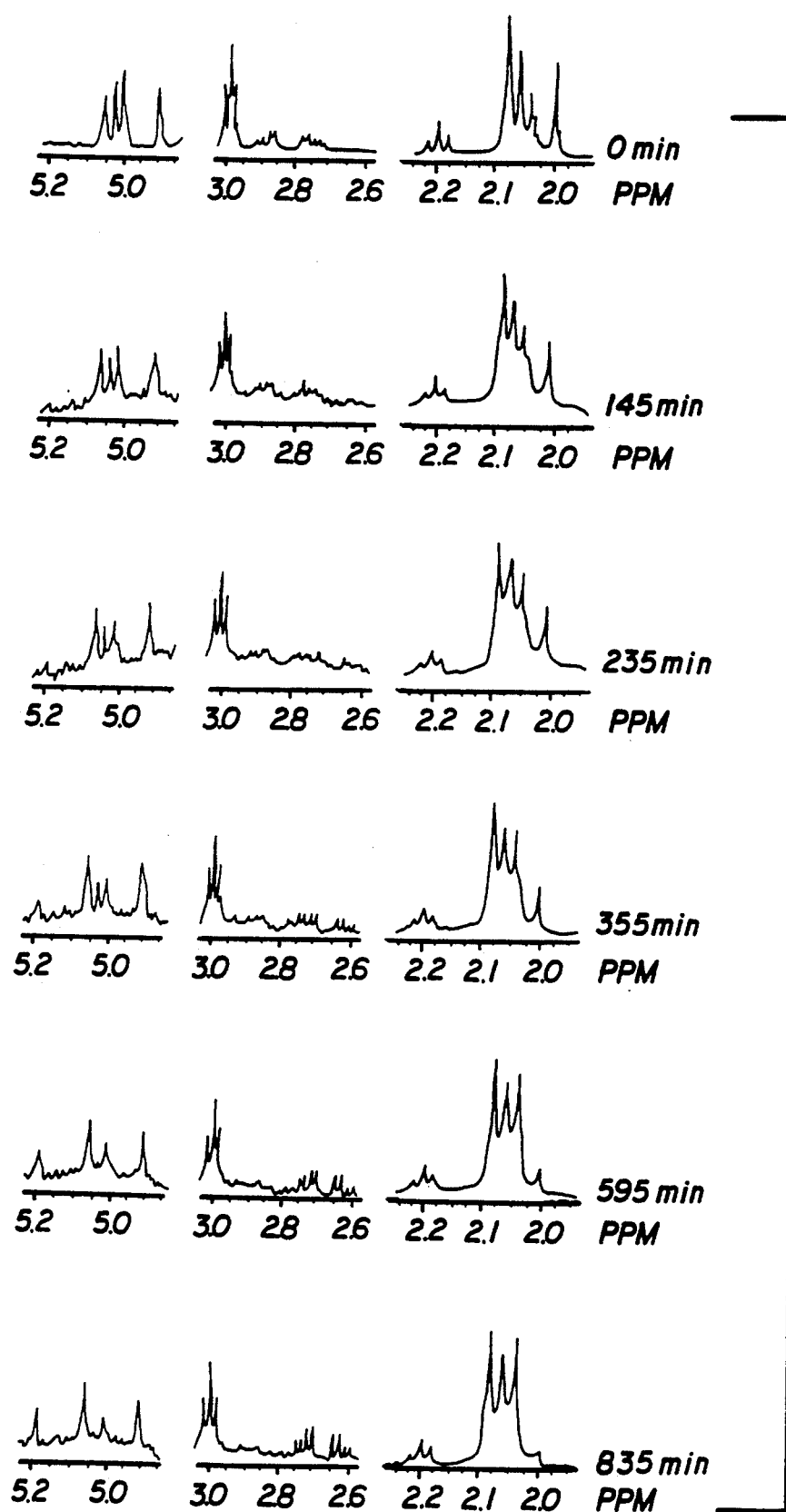
FIG. 6 illustrates the hydrolysis of turkey ovomucoid glycopeptide by aspartyl N-acetyl glycosylamine amidohydrolase from almond emulsin. Portions of $^1$H NMR spectrum recorded at six time points in the reaction are plotted (not to scale). The NMR signals for the anomeric proton (5.020 ppm) and N-acetyl group (2.000 ppm) of the N-acetylglucosamine-oligosaccharide attached to the asparagine residue and for the two beta-protons of asparagine (2.893 and 2.766 ppm) decrease in intensity as the hydrolysis reaction proceeds. At the same time, NMR signals appear for the N-acetyl group (2.037 ppm) in the reducing and residue of the free carbohydrate moiety and for the two beta-protons of aspartic acid (2.730 and 2.620 ppm) formed during the hydrolysis reaction. The NMR signal at 5.188 ppm is the anomeric proton of the alpha-anomer of the final equilibrated product; the appearance of the signal is delayed, consistent with the enzyme-catalyzed formation of a 1-amino-1-deoxyoligosaccharide which undergoes a subsequent nonenzymatic hydrolysis with release of ammonia.

The $^1H$ NMR spectrum of 2-acetamido-2-deoxy-D-glucose was recorded in order to model the (temperature-dependent) chemical shifts that were likely for the sugar at the reducing end of the new oligosaccharide that was produced during the enzyme-catalyzed hydrolysis reaction. The chemical shifts observed were 2.043 ppm for the N-acetyl group and 5.195 ppm ($J_{1,2}=3.58$ Hz) and 4.709 ppm ($J_{1,2}8.40$ Hz) for the anometric proton, the former the alpha-anomer and the latter the beta-anomer. The carbohydrate moiety of the turkey ovomucoid glycopeptide that is isolated from the first domain is a complex-type oligosaccharide. Spectra from a typical hydrolysis reaction of turkey ovomucoid glycopeptide incubated with the almond amidohydrolase and followed by $^1H$ NMR are shown in FIG. 6. The anomeric proton and the N-acetyl group for the N-acetylglucosamine-oligosaccharide attached to asparagine in the turkey ovomucoid glycopeptide have $^1H$ NMR chemical shifts of 5.020 ppm ($J_{1,2}=9.56$ Hz) and 2.000 ppm, respectively and the two beta-protons of asparagine have $^1H$ NMR chemical shifts of 2.766 ppm and 2.893 ppm. Other $^1H$ NMR signals observed in FIG. 6 are for the anomeric protons of mannose-4 (5.058 ppm) and mannose-4' (5.018, 5.0097, 4.908 ppm), for the ε-methylene protons of lysine (3.003 ppm, J=7.32 Hz), for the γ-methylene protons of glutamic acid (2.204 ppm, J=7.98 Hz), and for the N-acetyl groups (2.081–2.0229 ppm) of the turkey ovomucoid glycopeptide. During the hydrolysis reaction, the N-acetyl signal of 2.000 ppm, the beta-proton signals of asparagine at 2.766 and 2.893 ppm, and the anomeric proton signal at 5.020 ppm decrease simultaneously as the glycopeptide is hydrolysed by the enzyme, while at the same time signals at 2.037 ppm as well as at 2.620 and 2.730 ppm appear. A new $^1H$ NMR signal also appears at 5.188 ppm, but its appearance is delayed. Based on the model sugar compound, the NMR signals at 2.037 and 5.188 ppm have been assigned to the N-acetyl group and the anomeric proton (alpha-anomer), respectively, of the N-acetylglucosamine-oligosaccharide in the free carbohydrate moiety. The NMR signals at 2.620 and 2.730 ppm are assigned to the two beta-protons of aspartic acid in the polypeptide chain. The eight $^1H$ NMR signals at 2.000 ppm, 2.766 ppm, 2.893 ppm, 5.020 ppm, 2.037 ppm, 2.620 ppm, 2.730 ppm, and 5.188 ppm were all used to follow the course of the reaction. The delayed appearance of the $^1H$ NMR signals at 5.188 ppm was consistent with the formation of a 1-aminooligosaccharide intermediate in the hydrolysis reaction. A 1-aminooligosaccharide intermediate would be expected to have distinct $^1H$ NMR signals for the anomeric proton and for the N-acetyl group of the sugar bearing the 1-amino group. However, no $^1H$ NMR signal for the anomeric proton of a 1-aminooligosaccharide intermediate could be detected and the $^1H$ NMR signals for the N-acetyl group did not change following the appearance of the signal at 2.037 ppm. The latter observation was consistent with the formation of a 1-aminooligosaccharide intermediate, providing that the chemical shifts for the N-acetyl group in the intermediate and in the N-acetylglucosamineoligosaccharide, were nearly identical. To test these possibilities, we utilized 1-amino-1-dideoxy-N-acetylglucosamine as a model compound for the hydrolysis of the probable 1-aminooligosaccharide intermediate formed in the apparent two-step enzyme-catalyzed hydrolysis reaction.

The rate of hydrolysis for the model compound was readily measured using $^1$H NMR. Upon hydrolysis, the $^1$H NMR signal for the anomeric proton of the model compounded shifts downfield from 4.189 ppm ($J_{1,2}=9.35$ Hz) to 5.195 ppm ($J_{1,2}=3.38$ Hz), and 4.709 ppm ($J_{1,2}=3.38$ hz), the former the alpha-anomer and the latter the beta-anomer of the product, N-acetyl-glucosamine, while the chemical shift of the N-acetyl group is unchanged. The pseudo-first order rate constant for the enzyme-catalyzed reaction and for the hydrolysis of the model compound are given in Table I; based on the least squares standard error analysis, the precision in the pseudo-first order rate is ±5%. These limited data give energies of activation for the enzyme-catalyzed reaction of 9.5 kcal mol$^{-1}$ and for the model compound of 17.7 kcal mol$^{-1}$.

TABLE I

Pseudo-first order rate constants for hydrolysis reactions at p$^2$H 7.0.

| Temperature (min$^{-1}$) °C. | 1-Amino-N-acetyl-glucosamine 10 × k (min$^{-1}$) | Enzyme ug | Turkey ovomucoid glycopeptide $10^3$ × k |
|---|---|---|---|
| 22 | 0.88 | | |
| 24 | (1.08)* | 37.5 | 1.05 |
| 37 | 3.81 | 37.5 | 1.91 |
| | | 75.0 | 2.80 |
| | | (1200. | 61.1)* |
| 39 | (4.56)* | 50.0 | 3.19 |
| | | (37.5 | 2.39)* |

*Calculated

EXAMPLE 2

Trapping of the 1-Amino-1-Deoxyoligosaccharides Released from Turkey Ovomucoid Glycopeptide A solution of 1 mg of turkey ovomucoid glycopeptide in 0.4 ml of 50 mM phosphate, p$^2$H 7.0 buffer in 99.96% $^2$H$_2$O was equilibrated at 37° C. in a water bath. Enzyme (1.2 mg in 0.1 ml of buffer) was added and the solution was incubated at 37° C. The hydrolysis reaction was checked by $^1$H NMR. At the end of the incubation, acetic anhydride (5–10 ul) was added to trap the intermediate as the b 1-acetamido-N-acetylglucosamine-oligosaccharide and to quench to enzyme activity. The solution was applied to Bio-Gel P-4 column (104×3 cm) and equilibrated with double-distilled, de-ionized water at room temperature. Three ml fractions were collected and monitored for the presence of polypeptide by measuring A$_{280}$nm and for carbohydrate by the phenolsulfuric acid method. The carbohydrate-containing fractions were lyophilized and equilibrated with deuterium oxide: 3 times in 99.5% $^2$H, 2 times in 99.96% $^2$H, and 2 times in 99.996% $^2$H$_2$O for 24 h each followed by lyophilization. The $^1$H NMR of the carbohydrates was recorded in 99.996% $^2$H$_2$O. A standard reference compound was prepared by reacting acetic anhydride with 1-amino-1-dideoxy-N-acetylglucosamine in 99.996% $^2$H$_2$O to give 1,2-diacetamido-1,2-dideoxy-beta-D-glucopyranose. The $^1$H NMR signal for the anomeric proton moved downfield from 4.189 ppm ($J_{1,2}=9.35$ Hz) to 5.053 ppm ($J_{1,2}=9.33$ Hz) upon acetylation of the model compound and the 2-acetamido group moved upfield from 2.047 ppm to a position where the two acetamido groups had chemical shifts of 2.011 and 2.009 ppm; the coupling constant for the anomeric proton indicates that, as expected, the 1-amino compound retained the beta-conformation upon acetylation.

Figure 7A:
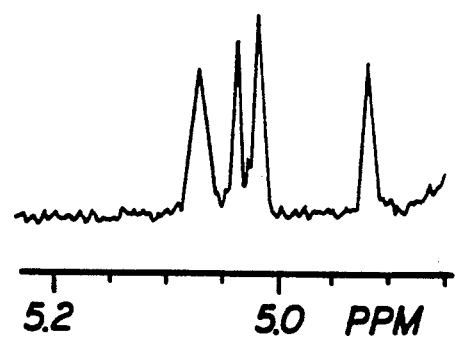
FIGS. 7A–7D illustrate trapping of the 1-amino-1-deoxyoligosaccharide that is formed in the reaction of betaaspartyl N-acetylglycosylamine amidohydrolase with turkey ovomucoid glycopeptide.
Figure 7B:
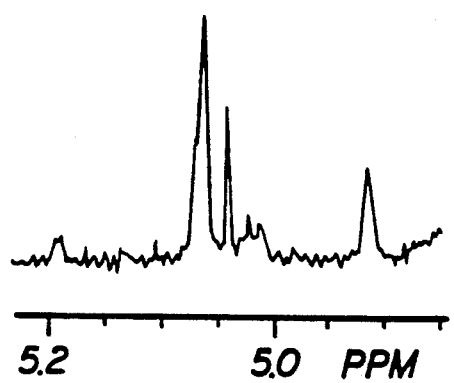
Figure 7C:
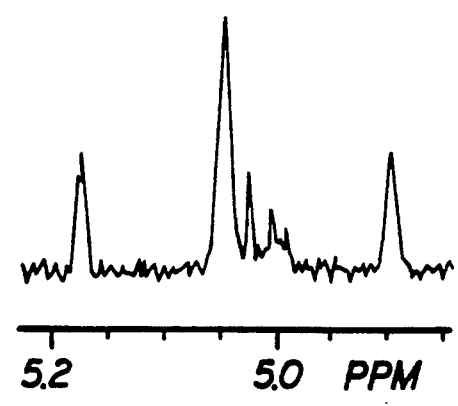
Figure 7D:
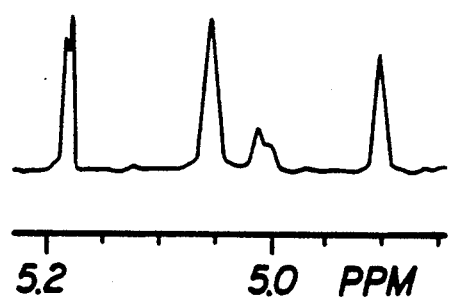
Figure 9A:
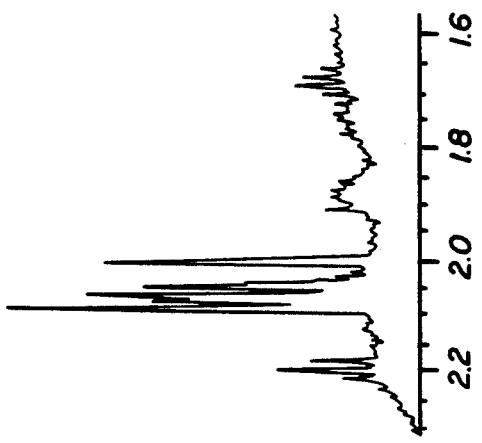
FIG. 9A is an $^1$H-NMR spectrum recorded at times 5.4–5.0 minutes for hydrolysis of turkey ovomucoid glycopeptide by aspartyl N-acetylglycosylamine amidohydrolase from *Flavobacterium meningosepticum.*
Figure 9C:
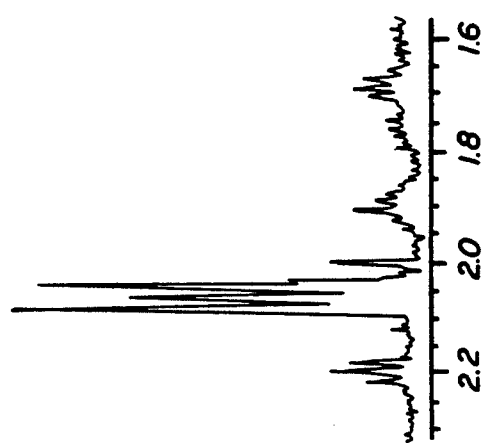
FIG. 9C is an $^1$H-NMR spectrum recorded at times 5.4–5.0 minutes for hydrolysis of turkey ovomucoid glycopeptide by aspartyl N-acetylglycosylamine amidohydrolase form *Flavobacterium meningosepticum.*
Figure 9B:
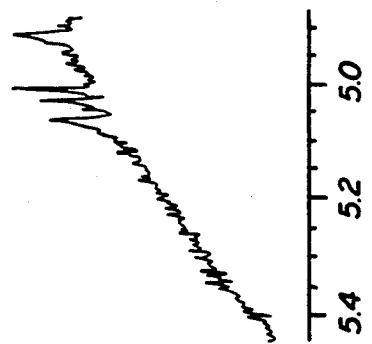
FIG. 9B is an $^1$H-NMR spectrum recorded at times 2.2–1.6 minutes for hydrolysis of turkey ovomucoid glycopeptide by aspartyl N-acetylglycosylamine amidohydrolase from *Flavobacterium meningosepticum.*
Figure 9D:
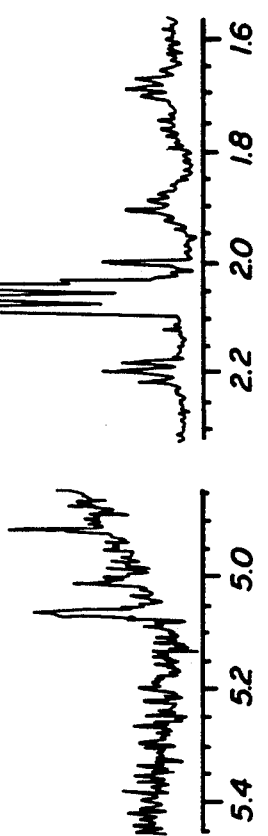
FIG. 9D is an $^1$H-NMR spectrum recorded at times 2.2–1.6 minutes for hydrolysis of turkey ovomucoid glycopeptide by aspartyl N-acetylglycosylamine amidohydrolase from *Flavobacterium meningosepticum.*
Figure 8A:
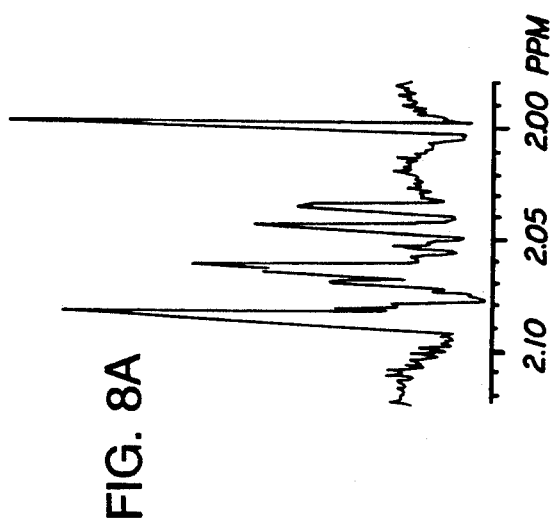
FIGS. 8A–8B illustrate the N-acetyl groups of the carbohydrate moiety of turkey ovomucoid glycopeptide (A) and the 1-acetamido derivative formed when the hydrolysis reaction is quenched with acetic anhydride after 1 h incubation (B).
Figure 8B:
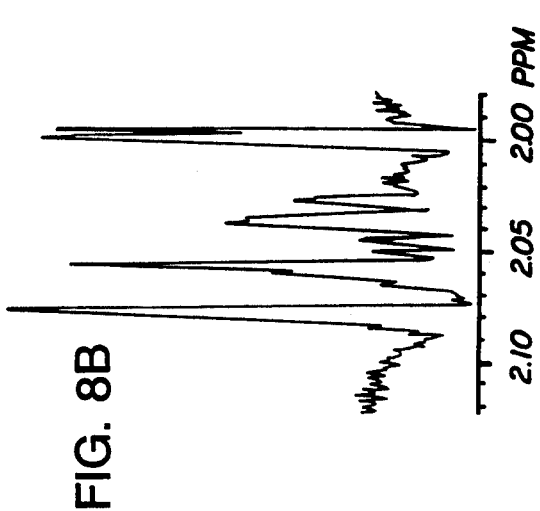

The anomeric protons for mannose-4 (5.058 ppm; $J_{1,2}=9.56$ Hz) and mannose-4' (5.018, 5.007, 4.908 ppm) in turkey ovomucoid glycopeptide are shown in FIG. 7A. When the glycopeptide was incubated at p$^2$H 7.0 and 37° C. with almond amidohydrolase and the reaction was quenched with acetic anhydride after 1-h (FIG. 7B), 2-h, and 4-h (FIG. 7C) incubation times, the $^1$H NMR signal of the anomeric proton for the reducing end N-acetylglucosamine-oligosaccharide for the isolated carbohydrate moiety was shifted downfield to 5.045 ppm ($J_{1,2}=9.81$ Hz); the signal partially overlaps the $^1$H NMR signal of the anomeric proton for mannose-4. The $^1$H NMR signal of the alpha-anomer of the N-acetylglucosamine reducing end in the final carbohydrate product appears at 5.188 ppm ($J_{1,3}=2.27$ Hz). Based on the model compound, the NMR signal at 5.045 ppm is the anomeric proton of acetylated 1-aminooligosaccharide in the beta-conformation—the postulated intermediate. The $^1$H NMR spectra were integrated and the amounts of the acetylated 1-aminooligosaccharide and the final carbohydrate product were calculated as a percentage (±5%) of the total isolated product. The theoretical percentages of the products expected were calculated from the kinetic data using the differential equations (Equation 3) for the two-step reaction. After a 1-h reaction time, 82% of the product was trapped as the intermediate and 18% was present as the final carbohydrate product. Consistent with this, the predicted quantities were 3% glycopeptide (not hydrolyzed by enzyme), 82% intermediate, and 15% final product. After a 2-h incubation before trapping, the product was a mixture of 72% intermediate and 28% completely hydrolyzed carbohydrate (67% of the intermediate and 32% of the final product were expected on the basis of out kinetic model). Finally, after 4-h reaction time before trapping, the intermediate represented 40% and the free carbohydrate was 60% of the total product (the predicted quantities were 43% and 57% respectively). The $^1$H NMR spectrum of the same region in the completely hydrolyzed and equilibrated carbohydrate moiety shows resonance signals of the anomeric protons for the alpha-anomer of the reducing end N-acetylglucosamine, the mannose-4, and the mannose 4' (FIG. 7D). The $^1$H NMR signal of the N-acetyl group of N-acetylglucosamineoligosaccharide attached to asparagine in the glycopeptide appears at 2.000 ppm (FIG. 8A). The $^1$H NMR spectrum of the N-acetyl group of the acetylated carbohydrate moiety after 1-h incubation is shown in FIG. 8B. The two $^1$H NMR signals that appear at 2.000 and 2.002 ppm are those of the two N-acetyl groups at the reducing end of the sugar. The $^1$H NMR spectra of the N-acetyl groups recorded after 2-h and 4-h reaction times showed that the two signals at 2.000 and 2.002 ppm had decreased in magnitude, while a $^1$H NMR signal appeared at 2.037 ppm. Thus the $^1$H NMR data for the trapping experiment give a clear, direct indication that 1-aminooligosaccharide is formed as in intermediate in the almond amidohydrolase-catalyzed hydrolysis of turkey ovomucoid glycopeptide.

EXAMPLE 3

Release of 1-amino-1-deoxyoligosaccharides from turkey ovomucoid glycopeptide with aspartyl N-acetylglycosylamine amidohydrolase from Flavobacterium meningoseptimum To a solution of 0.7 mg of TOG in 50 mM phosphate, $p^2H$ 8.0 buffer in 99.96% $^2H_2O$ equilibrated at 37° was added 2 units of N-Glycanase TM (Genzyme, Boston, Mass.) to give a final reaction volume of 58 ul. The reaction was followed by $^1H$-NMR as described for the almond emulsin enzyme reaction.

The hydrolysis of the TOG was followed by disappearance of the $^1H$-NMR signal for the N-acetylglucosylamine group linked to the asparagine residue. The production of the released 1-amino-1-deoxyoligosaccharides was followed by monitoring the appearance of the actyl signal at 2.037 ppm. Under the conditions of the reaction, the hydrolysis of TOG was approximately 80% complete after 36 h (FIG. 9). The reaction can be accelerated by the addition of greater units of enzyme.

Unlike the reaction performed at pH 7.0 in Example 1, the released beta-1-amino-1-deoxyoligosaccharide is stable at pH 8. Thus even after 36 h there is no appreciable $^1H$-NMR signal for the alpha-anomer (5.19 ppm) of hydrolyzed aminodeoxysugar.

As in Example 1, the 1-amino-1-deoxyoligosaccharide was trapped by the addition of acetic anhydride.

EXAMPLE 4

Trapping of Glycosylamines with Dansyl Chloride

The practicality of trapping the glycosylamines with dansyl chloride was investigated with the model compound 2-acetamido-1-amino-1,2-dideoxyglucose. The aminodeoxysugar (44 mg) in 2 ml of 0.2M $NaHCO_3$ was mixed with 1.1 ml of acetone containing dansyl chloride (60 mg). The reaction mixture was heated with stirring at 70° for 2 h. At the completion of the reaction a homogeneous solution was obtained, with only a trace of the original yellow color remaining. Analysis of the reaction mixture by silia gel thin-layer chromatography (methylene chloride/methanol, 5/1 by vol) indicated the presence of the following reaction components: dansyl chloride (rf 0.99), dimethylaminonaphthalene sulfonamide (rf 0.95), dimethylaminonaphthalene sulfonic acid (rf 0.34), a trace of 2-acetamido-1-amino-1,2-dideoxy-glucose (rf 0.06), and a new product (rf 0.55). The reaction product corresponding to the spot at rf 0.55 was purified by silica gel chromotography (2×15 cm column, eluted with methylene chloride/methanol, 6/1 by vol.). A portion of the desired product was obtained free of contaminants (the elution volume of this product was 100-110 ml). After concentration under reduced pressure, 12 mg of a yellow glassy solid was obtained. $^1H$-NMR analysis confirmed that the material was the expected 2-acetamido-1,2-dideoxy-1-dimethylaminonaphthalene-B-D-glucose: 1.50 (s, 3H, $CH_3$—C—NH), 2.85 (s, 6H, $(CH_3)_2$—N), 3.10–3.90 (m, 6H, pyranose ring protons), 4.55 (d, 1H, anomeric, J=9.4 Hz), 7.27–7.59 (m, 3H, aromatic), and 8.25–8.54 (m, 3H, aromatic). There appeared to be a small amount (<5%) of the alpha-anomer (δ5.10) present in the isolated product. The UV spectrum of the product gave two absorbance peaks (EtOH) with $\lambda_{max}$ at 251 nm and 336 nm.

EXAMPLE 5

Synthesis of the PITC Derivatives of the 1-Amino-1-Deoxyoligosaccharides Obtained from Hen Ovomucoid Glycopeptide (HOG) by Digestion with PNGase F The tryptic HOG substrate, which contained the glycosylation site Asn-53, was prepared according to the procedure of Yet et al., op. cit. HOG (10.3 mg) was added to 60 U of PNGase F (N-Glycanase enzyme, Genzyme) in 600 microliters of 0.2 M sodium phosphate, pH 7.5, and incubated at 37° C. for four hours. At the end of this time the amidase reaction was 85% complete as judged by hplc analysis. The reaction mixture was frozen and lyophilized. The lyophilized solid was dissolved in 500 microliters of water and mixed with a solution of phenyl isothiocyanate (500 microliters) and triethylamine (500 microliters) in 3.5 milliliters of methanol.

The reaction mixture was stirred at 20° C. for 1 hour and then extracted with four 6 mL portions of chloroform. The aqueous layer was separated from a precipitate and the organic layer passed through a 10 mL column of Amberlite MB 3 resin. The flow through and washings were freeze dried.

EXAMPLE 6

Synthesis of the CBI Derivative of 1-Amino-1-Deoxy-N-Acetylglucosamine

Figure 10:
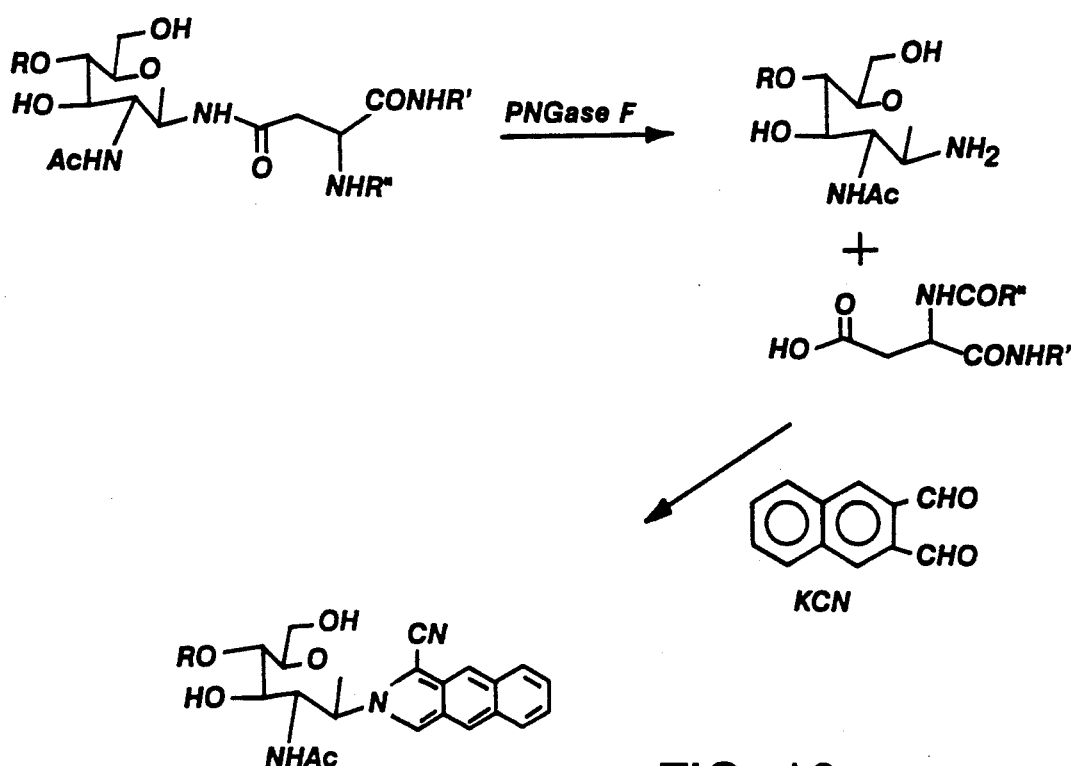
FIG. 10 is a scheme for the formation of cyanobenz-[f]isoindole (CBI) derivatives of 1-amino-1-deoxyoligosaccharides released from glycoproteins and glycopeptides by PNGase.

The general scheme for formation of a CBI derivative is shown in FIG. 10. To a suspension of 2,3-naphthalenedicarboxaldehyde (Molecular Probes, 21 mg, 0.114 mmol) in methanol (2 ml) was added a solution of KCN (8.8 mg, 0.136 mmol) in $H_2O$ (0.14 ml). The resultant yellow solution was allowed to stir at 20° C. for 1 min. To this solution was added 1-amino-1-deoxy-GlcNAc (Aldrich, 25 mg, 0.114 mmol) as a solid. The reaction mixture was stored at 0° C. overnight, after which time it had turned a reddish-brown color. The reaction mixture was concentrated in vacuo to give a dark red oil. The oil was dissolved in a 6:1 $CH_2Cl_2$:MeOH solvent system to provide 12.3 mg (28%) of the desired product as a yellow oil. The CBI derivative of 1-amino-deoxy GlcNAC was analyzed by Hplc, UV, $^1H$-NMR and MS. Hplc analysis was performed with a $C_{18}$ Novapak column. The mobile phase was a 10 minute gradient of 100% Solvent A to 75% Solvent A/25% Solvent B followed by a 1 minute hold. Solvent A was 80% acetonitrile/20% water and Solvent B was 100% acetonitrile. The flow rate was 1 mL/min and detection was performed with a fluorescence detector ($_{ex}$ 250 nm, $_{em}$ 490 nm). The retention time of the CBI derivative as 10.7 minutes. The compound exhibited a $UV_{max}$ (in $H_2O$) at 402, 424, and 446 nm. The $^1H$-NMR spectra gave: 8.16, 2H, doublet; 7.71, 1H singlet; 7.60, 1H doublet; 7.44, 1H, doublet; 7.30, 1H, triplet; 7.19, 1H, triplet; 4.31, 1H, doublet; 4.0–3.2, 5H, multiplet; 1.92, 3H, singlet.

EXAMPLE 7

High Mannose CBI Standards. Synthesis of the CBI Derivatives of the 1-amino-1-deoxyoligosaccharides obtained from Endo H treatment of Soybean 7S Globulin To a solution of 2,3-naphthalenedicarboxaldehyde (1.2 mg, 5.9 umole, Molecular Probes), in methanol (1.5 ml) was added synthetic 1-amino high-mannose oligosaccharide (Man$_{6-8}$GlCNAc$_1$-NH$_2$) (8.4 mg, 5.6 umol) in a solution of 50 mM sodium phosphate, pH 8.0, buffer (2.0 ml). The reaction mixture was allowed to stir for 30 minutes at 20° C. before adding a solution of KCN (0.4 mg, 5.9 umol) in 50 mM sodium phosphate, pH 8.0, buffer (20 ul). The methanolic mixture of NDA/CN was allowed to stir at 20° C. for 1 minute. The glycosylamines were synthesized using Endo-H released high-fraction oligosaccharides from soybean 7S globulin protein fraction. The resultant highly fluorescent reaction mixture was allowed to stir at 20° C. for 1 h prior to hplc analysis. Purification of the fluorescent CBI-oligosaccharide derivatives was effected by gel filtration (Biogel P2).

EXAMPLE 8

Synthesis of the CBI Derivative of 1-Amino-1-Deoxyoligosaccharides Obtained from the Digestion of RNase B with PNGase F Type B RNase B (1 mg, from Sigma) in a 3.5 mM 2-mercaptoethanol solution (250 ul) was placed in boiling water for 5 minutes and then kept at 37° C. for 1 hr to reduce the protein's disulfide bridges and make it susceptible to N-glycanase enzyme digestion. Excess reductant was removed by repeated filtration and dilution (5×1 ml) of the protein solution using an Amicon 10 Kd mol. wt. filtration device.

To the resultant RNase B solution (250 ul) was added H$_2$O (442 ul), 0.1 M sodium phosphate, pH 8.6 buffer (200 ul) and 100 units of recombinant N-glycanase in 20 mM sodium phosphate, pH 8.6 (108 ul) to give a final volume of 1 ml of 20 mM sodium phosphate, pH 8.6 buffer. The N-glycanase hydrolysis mixture was incubated at 37° C. for 1 h, at which time SDS/PAGE indicated that deglycosylation of RNase B was essentially complete. The reaction mixture was immediately filtered through an Amicon (10 Kd cut-off) device to separate ht residual high-molecular weight protein species (RNAase B and N-glycanase) from the released 1-amino-1-deoxy-oligosaccharide intermediates (Man$_5$-$_8$GlcNAc$_2$-NH$_2$). To the filtrate (800 ul), which was estimated to contain ~30 ug(~23 nmols) of the released 1-amino-1-deoxyoligosaccharides was added a freshly prepared, 70% aqueous MeOH solution (25 ul) containing 2,3-naphthalenedicarboxaldehyde (8.6 ug, 50 nmol) and KCN (3.1 ug, 50 nmol). The resultant yellow, highly fluorescent reaction mixture was stirred at 20° C. room temperature for 1 h prior to hplc analysis. Purification of the NDA labeled RNase B oligosaccharides was effected by gel filtration (Biogel P2).

EXAMPLE 9

Figure 11:
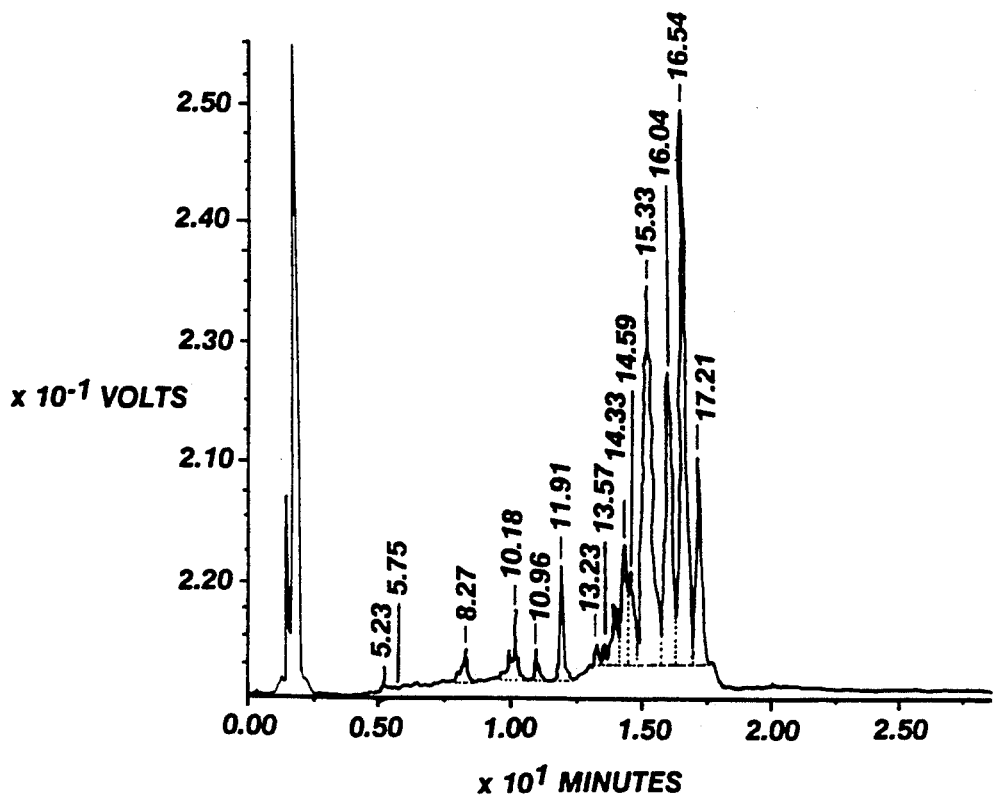
FIG. 11 shows the HPLC fractionation of PITC-labeled 1-amino-1-deoxyoligosaccharides derived from hog ovomucoid glycopeptide on a TSK AK-5 column. The mobile phase was a 20 minute gradient beginning with 80% acetonitrile/20% water and ending with 10% acetonitrile and 90% water. The flow rate was 2 mL/min and the eluant was monitored with a UV spectrophotometer at 290 nm.

Fractionation of the PITC Derivatives of the 1-Amino-1-Deoxyoligosaccharides Obtained from Hen Oviduct Glycoprotein HPLC analysis was performed on the PITC derivatives described in Example 5 using a TSK Ax-5 column eluted with a 30 minute linear gradient from 80% acetonitrile/20% water to 10% acetonitrile/90% water. The flow rate was 2 mL/minute and detection was accomplished by measurement of absorbance at 280 nm. Peaks were observed at 13,57, 14.33, 14.59, 15.33, 16.04, 16.54 and 17.21 minutes at illustrated in FIG. 11.

EXAMPLE 10

Figure 12:
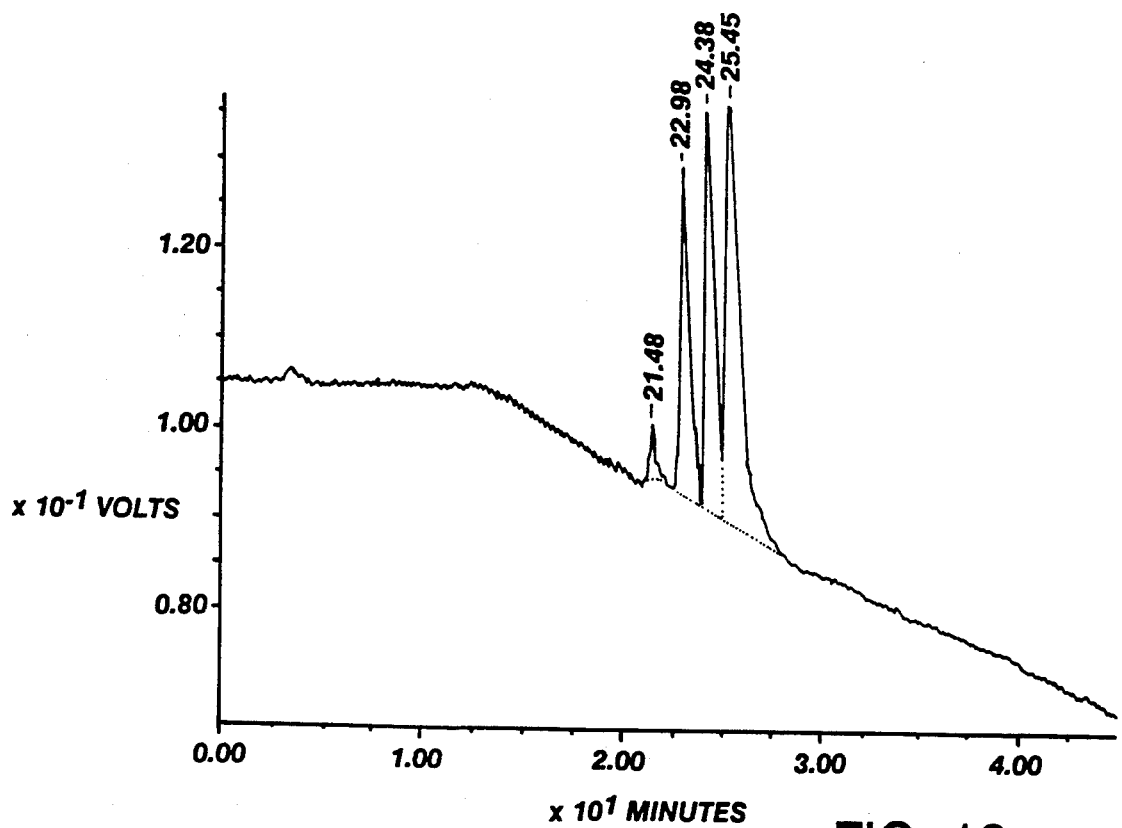
FIG. 12 shows the HPLC fractionation, on the TSK AX-5 column, of CBI-derivatives from synthetic high-mannose 1-amino-1-deoxyoligosaccharides from soybean 7S globulin protein. The mobile phase was a 40 minute gradient beginning with 80% acetonitrile/20% water and ending with 20% acetonitrile/80% water. The flow rate was 1.0 mL/min and the eluant was monitored with a fluorescence detector (excitation 250 nm, emission 490 nm).

Fractionation of the CBI Derivatives of the 1-Amino-1-Deoxyoligosaccharides Obtained from Soybean 7S Globulin Fraction HPLC analysis (AX-5 column, 1.0 m./min, 20% H$_2$O 80% CH$_3$CN to 90% H$_2$O/10% CH$_3$CN over 35 min) with fluorescence detection (250 nm excitation, 490 nm emission) of the sample described in Example 7 showed three major peaks with retention times of 24.3, 25.6, and 26.8 min in a 1:1.1:2.4 ratio respectively. The fluorescent hplc pattern of the NDA-CN labelled Man$_6$-$_8$GlcNAc isomers (FIG. 12) was very similar to the pattern of an hplc analysis of NaB[$^3$H]$_4$-reduced 7S globulin.

EXAMPLE 11

Fractionation of the CBI Derivatives of the 1-Amino-Deoxyoligosaccharides Obtained from RNase B.

Figure 13:
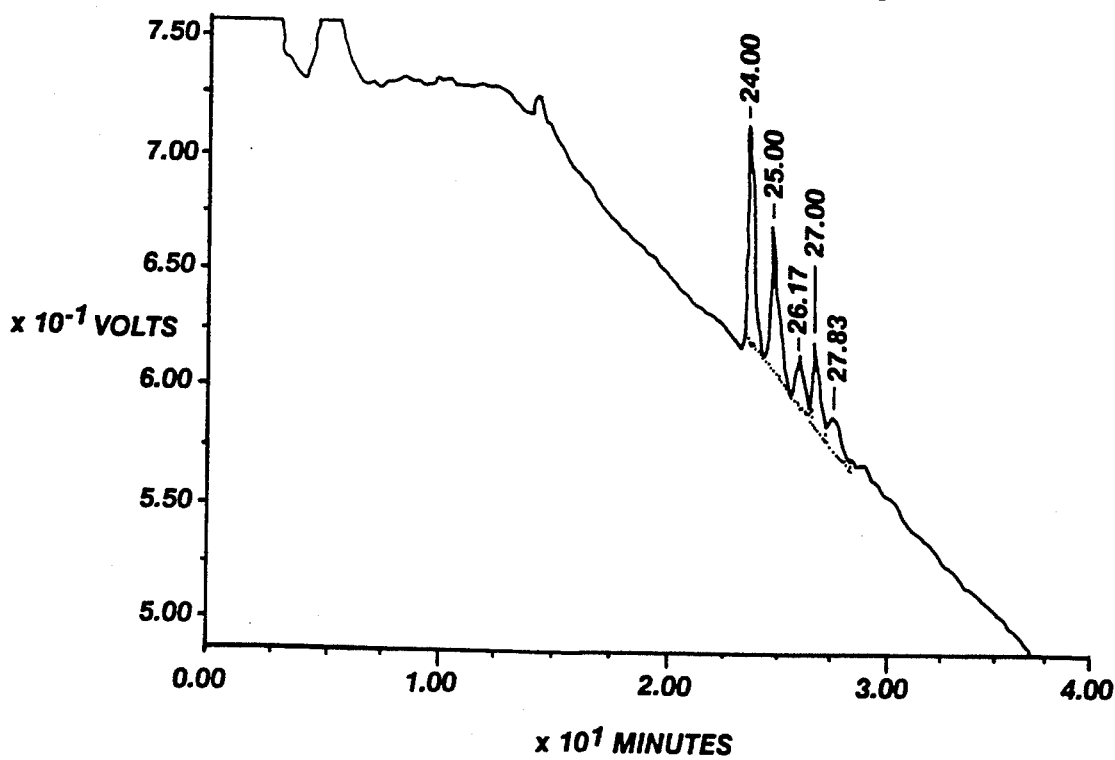
FIG. 13 shows the HPLC fractionation on a TSK AX-5 column of CBI derivatives of PNGase-produced high-mannose 1-amino-1-deoxyoligosaccharides from bovine RNase B. HPLC conditions were identical to those described in FIG. 12.

HPLC analysis (AX-5 column, 1.0 m./min, 20% H$_2$O 80% CH$_3$CN to 90% H$_2$O/10% CH$_3$CN over 35 min) with fluorescence detection (250 nm excitation, 490 nm emission) of the samples described in Example 8 showed five major fluorescent peaks with retention times of 24.0 min, 25.0 min. 26.2 min, 27.0 min and 27.8 min in a 2.5:2.1:1.2:1.2:1.0 ratio respectively. The fluorescent hplc pattern of the NDA-CN labelled material (FIG. 13) was similar to the pattern of an hplc analysis of NaB[$^3$H]$_4$-reduced RNase B oligosaccharides.

EXAMPLE 12

Figure 14:
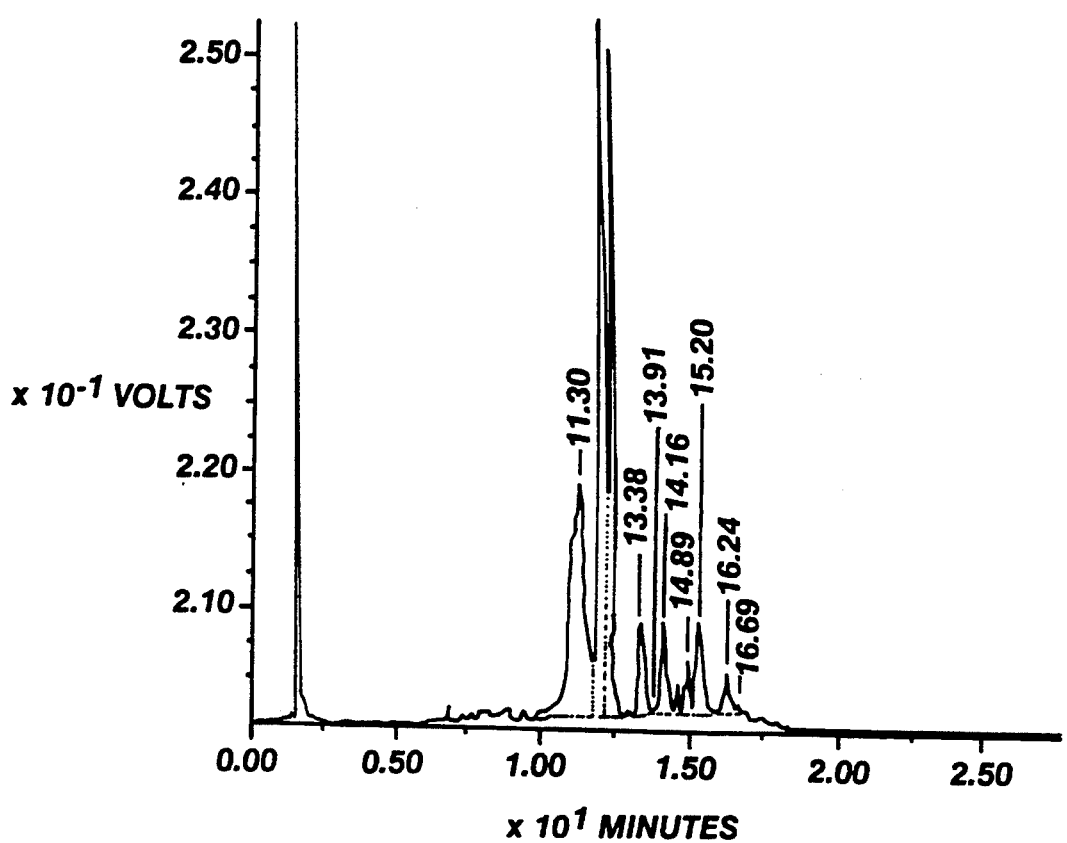
FIG. 14 shows the HPLC fractionation on a TSK AX-5 column of PITC-labeled 1-amino-1-deoxyoligosaccharides from FIG. 11 after treatment with jack-bean hexosaminidase enzyme.

Digestion of the PITC Derivatives of the 1-Amino-1-Deoxyoligosaccharides from HOG The sample of PITC-labeled 1-amino-1-deoxyoligosaccharides described in Example 5 was dissolved in 200 microliter 0.1 M citrate buffer, pH 5.0. A 46 microliter aliquot was removed. To the remaining solution was added 10 units of Jack bean $\beta$-hexosaminidase (Sigma) in 400 microliters of 0.1 M citrate buffer, pH 5.0 and 110 microliters of 100 mM galactonolactone. The reaction mixture was at 37° C. for 5 hours and then analyzed by hplc as illustrated in FIG. 14. Major peaks were observed at 11.30 and 12.04, and minor peaks at 13.38, 14.16, 15.28, and 16.24 minutes.

Other embodiments are within the following claims.

We claim:

1. A fluorescent 1-amino-1-deoxyoligosaccharide, said 1-amino-1-deoxyoligosaccharide being obtained by the cleavage of an Asn-linked oligosaccharide from a glycoprotein with aspartyl N-acetylglycosylamine amidohydrolase, wherein the Asn-linked amino group of said oligosaccharide is derivatized by reaction with a fluorescent reagent to form glycosylamine bond with the fluorescent reagent.

2. A fluorescent 1-amino-1-deoxyoligosaccharide, said 1-amino-1-deoxyoligosaccharide being obtained by the cleavage of an Asn-linked oligosaccharide from a glycoprotein with aspartyl N-acetylglycosylamine amidohydrolase, wherein the Asn-linked amino group of said oligosaccharide is derivatized by reaction with phenyl isothiocyanate.

3. A fluorescent 1-amino-1-deoxyoligosaccharide, said 1-amino-1-deoxyoligosaccharide being obtained by the cleavage of an Asn-linked oligosaccharide from a glycoprotein with aspartyl N-acetylglycosylamine amidohydrolase, wherein the Asn-linked amino group of said oligosaccharide is derivatized by reaction with naphthalene-2,3-dicarboxaldehyde and cyanide.

* * * * *